United States Patent [19]
Lin

[11] Patent Number: 6,080,367
[45] Date of Patent: Jun. 27, 2000

[54] AROMATIC CONTAINER

[76] Inventor: Jun-Ru Lin, 58, Ma Yuan West St., Taichung, Taiwan

[21] Appl. No.: 09/190,393

[22] Filed: Nov. 10, 1998

[51] Int. Cl.⁷ .................................................. A61L 9/04
[52] U.S. Cl. ..................... 422/124; 422/123; 422/305; 422/306; 422/120; D23/366; D23/367; 239/57; 239/60; 261/DIG. 17; 261/DIG. 65
[58] Field of Search .................................... 422/4, 5, 120, 422/123, 124, 305, 306; D23/366, 367; 392/386, 390; 55/385.1, 385.2, 385.3, 385.4; 239/57, 60; 261/DIG. 17, DIG. 65

[56] References Cited

U.S. PATENT DOCUMENTS

| | | | |
|---|---|---|---|
| 4,808,347 | 2/1989 | Dawn | 422/124 |
| 5,407,642 | 4/1995 | Lord | 422/120 |
| 5,695,692 | 12/1997 | Kennedy | 422/124 |
| 5,704,832 | 1/1998 | Borrell | 422/124 |
| 5,820,792 | 10/1998 | Lin | 422/124 |
| 5,932,147 | 8/1999 | Chen | 422/124 |

*Primary Examiner*—Terrence R. Till
*Assistant Examiner*—Fariborz Moazzam

[57] ABSTRACT

An aromatic container has a rotating device, a disk vessel disposed on the rotating device, a ring disposed on the disk vessel, a pivot seat engaging with the rotating device, and a clamp device engaging with the pivot seat. The ring has a plurality of lower columns, a plurality of circular apertures, and a center opening receiving a center cover.

3 Claims, 8 Drawing Sheets

AROMATIC CONTAINER

BACKGROUND OF THE INVENTION

The present invention relates to an aromatic container. More particularly, the present invention relates to an aromatic container which can be rotated.

A conventional aromatic container is disposed in a vehicle. However, the conventional aromatic container cannot be rotated. Aromatics are placed in the conventional aromatic container. After the aromatics are consumed completely, the conventional aromatic container is useless.

SUMMARY OF THE INVENTION

An object of the present invention is to provide an aromatic container which can be rotated.

Another object of the present invention is to provide an aromatic container which can refill aromatics.

Accordingly, an aromatic container comprises a rotating device, a disk vessel disposed on the rotating device, a ring disposed on the disk vessel, a pivot seat engaging with the rotating device, and a clamp device engaging with the pivot seat. The ring has a plurality of lower columns, a plurality of circular apertures, and a center opening receiving a center cover. The disk vessel has a central threaded aperture, a plurality of recesses receiving aromatics, a plurality of vent apertures, and a plurality of round apertures formed on an edge of the disk vessel. The round apertures receive the columns. The rotating device has a center hole. The pivot seat has a block, and a hollow post inserted in the center hole. The clamp device has a through hole receiving the block. A bolt passes through the central threaded aperture, the center hole, and the hollow post to fasten the disk vessel, the rotating device, and the pivot seat together.

In accordance with another preferred embodiment of the presenr invention, an aromatic container comprises a rotating device, a disk vessel disposed on the rotating device, a round cover disposed on the disk vessel, a pivot seat engaging with the rotating device, and a clamp device engaging with the pivot seat. The disk vessel has a central threaded aperture, a plurality of recesses receiving aromatics, a plurality of vent apertures, and a plurality of round apertures formed on an edge of the disk vessel. The round apertures receive the columns. The rotating device has a center hole. The pivot seat has a block, and a hollow post inserted in the center hole. The clamp device has a through hole receiving the block. A bolt passes through the central threaded aperture, the center hole, and the hollow post to fasten the disk vessel, the rotating device, and the pivot seat together.

DETAILED DESCRIPTION OF THE INVENTION

Figure 1:
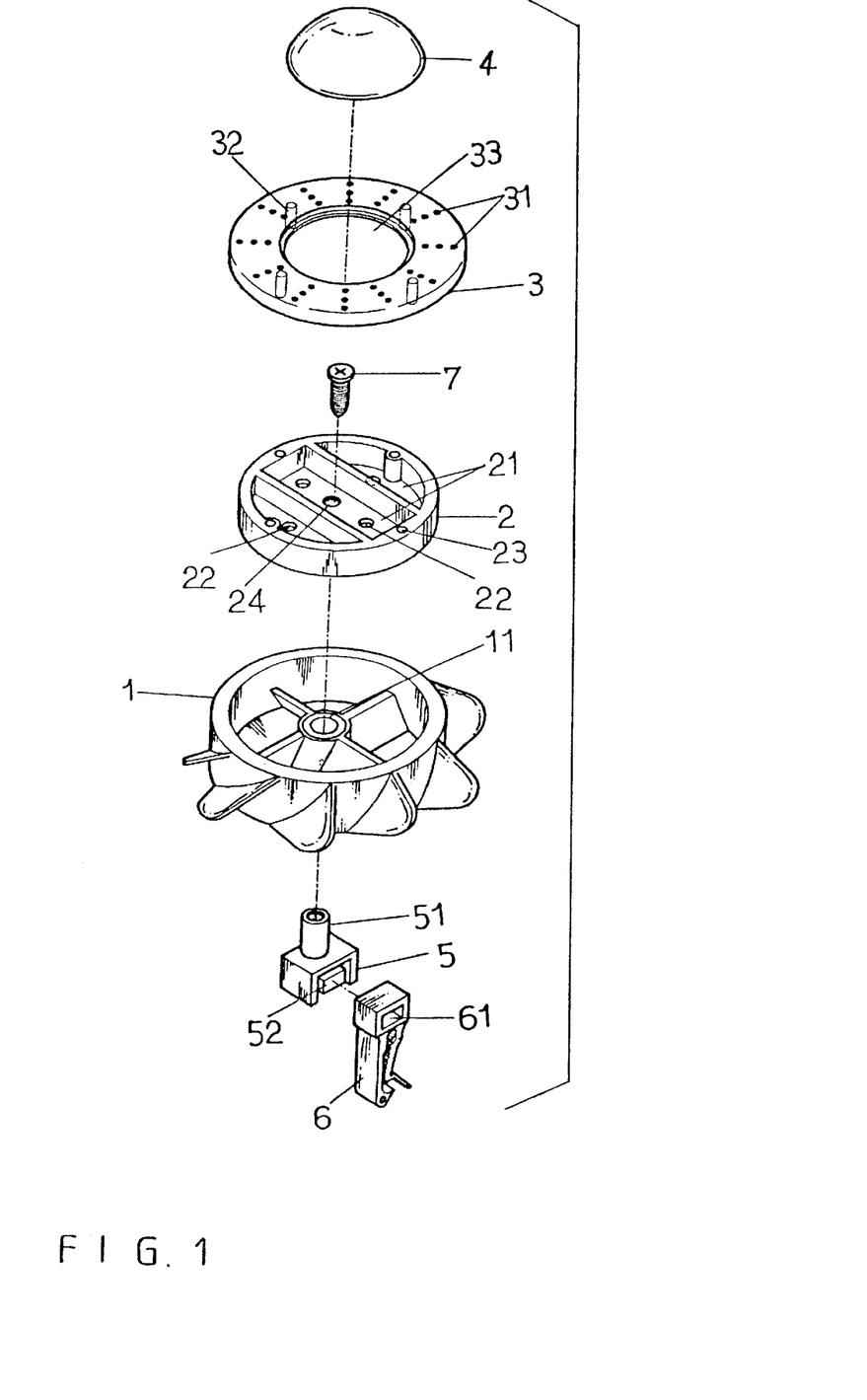
FIG. 1 is a perspective exploded view of an aromatic container of a preferred embodiment in accordance with the present invention.
Figure 2:
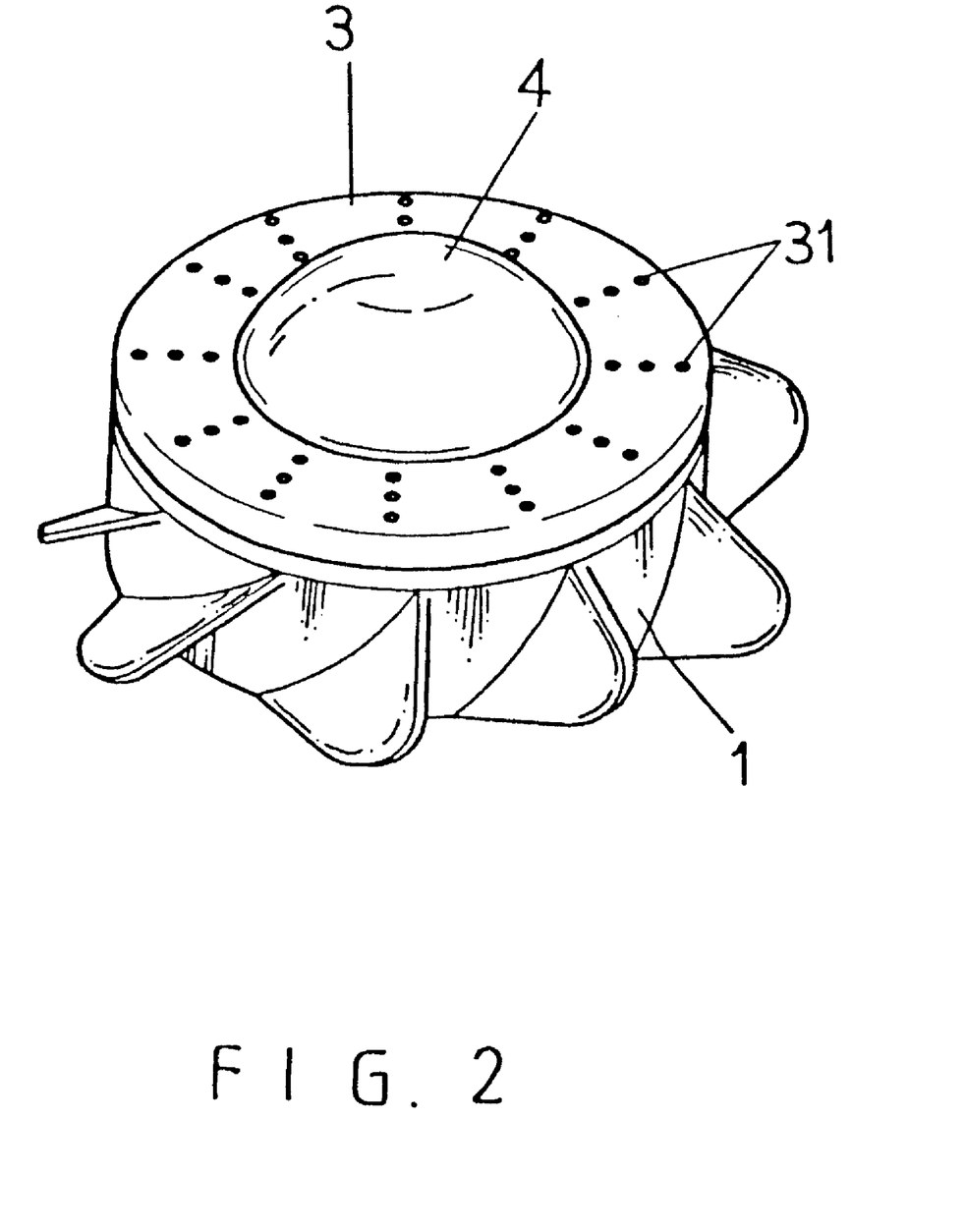
FIG. 2 is a perspective assembly view of an aromatic container of a preferred embodiment without a pivot seat and a clamp device.
Figure 4:
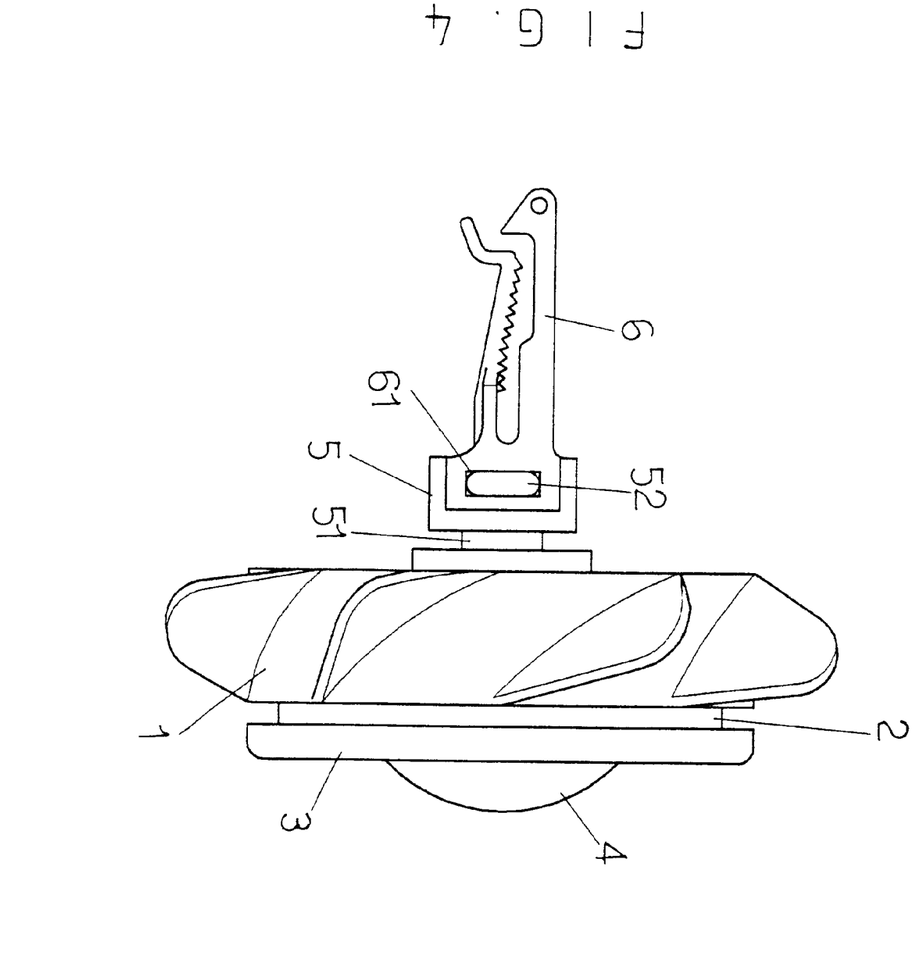
FIG. 4 is an elevational assembly view of an aromatic container of a preferred embodiment in accordance with the present invention.

Referring to FIGS. 1, 2 and 4, an aromatic container comprises a rotating device 1, a disk vessel 2 disposed on the rotating device 1, a ring 3 disposed on the disk vessel 2, a pivot seat 5 engaging with the rotating device 1, and a clamp device 6 engaging with the pivot seat 5.

The ring 3 has a plurality of columns 32, a plurality of circular apertures 31, and a center opening 33 receiving a center cover 4.

The disk vessel 2 has a central threaded aperture 24, a plurality of recesses 21 receiving aromatics (not shown in the figures), a plurality of vent apertures 22, and a plurality of round apertures 23 formed on an edge of the disk vessel 2. The round apertures 23 receive the columns 32.

The rotating device 1 has a center hole 11. The pivot seat 5 has a block 52, and a hollow post 51 inserted in the center hole 11.

The clamp device 6 has a through hole 61 receiving the block 52.

A bolt 7 passes through the central threaded aperture 24, the center hole 11, and the hollow post 51 to fasten the disk vessel 2, the rotating device 1, and the pivot seat 5 together.

Figure 1A:
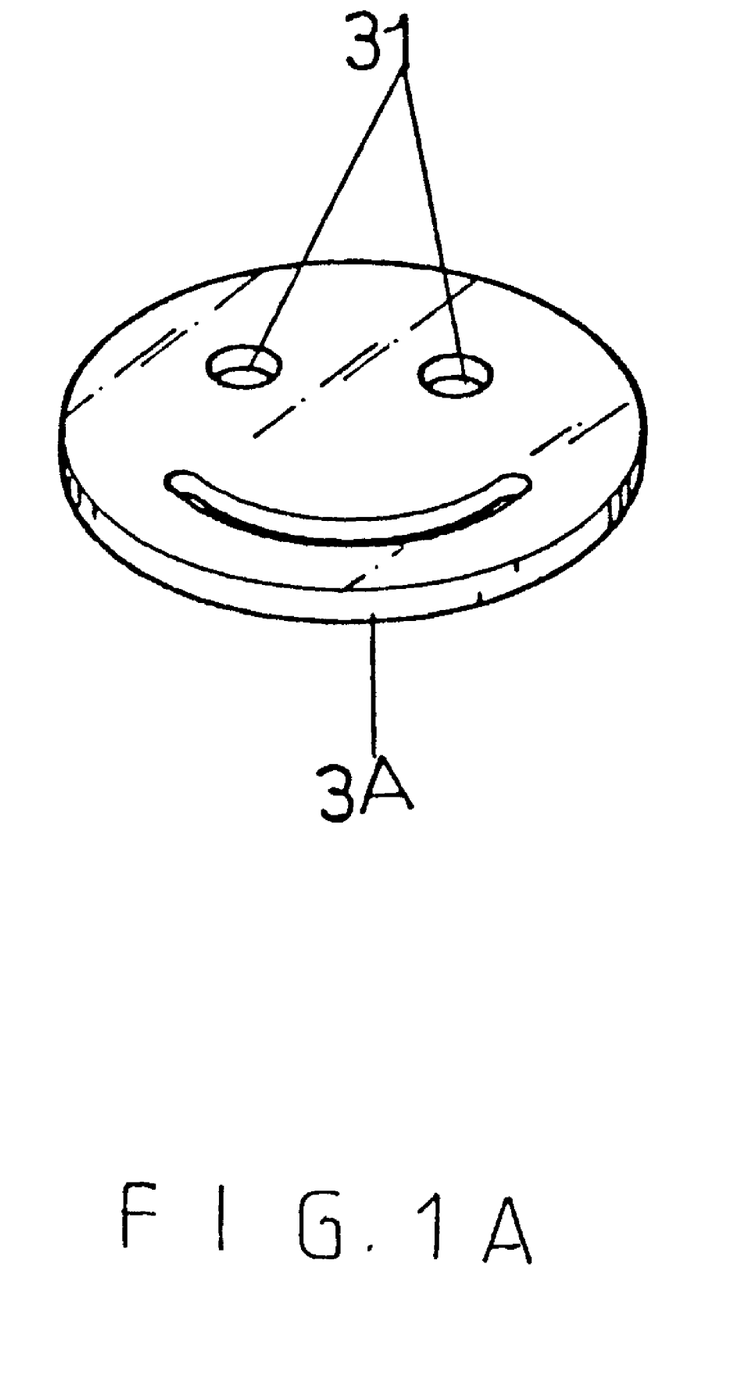
FIG. 1A is a perspective view of a round cover of a second preferred embodiment in accordance with the present invention.
Figure 2A:
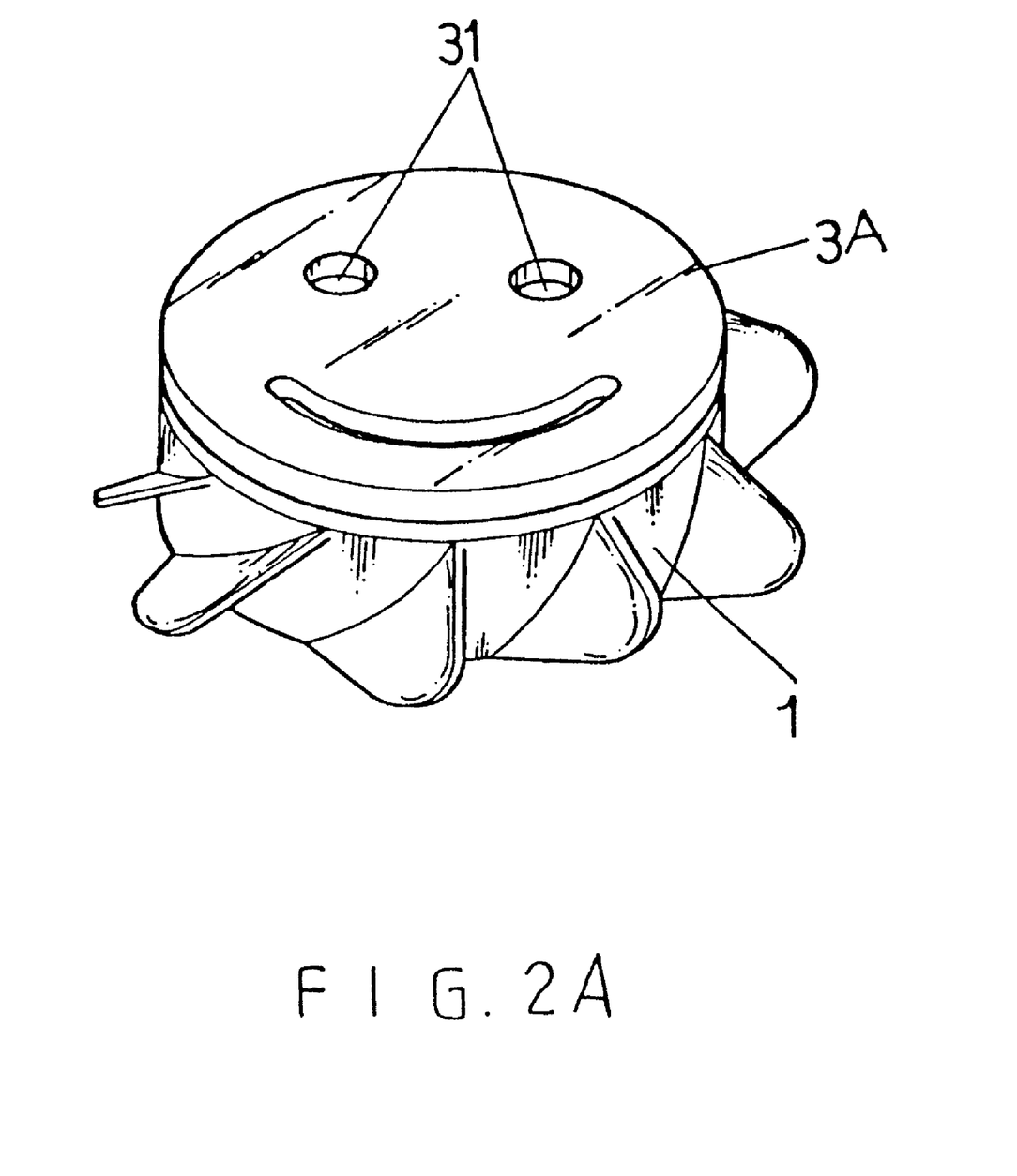
FIG. 2A is a perspective assembly view of an aromatic container of a second preferred embodiment without a pivot seat and a clamp device.

Referring to FIGS. 1A and 2A, another round cover 3A can replace the ring 3 and the center cover 4. The round cover 3A is disposed on the disk vessel 2. The round cover 3A has a plurality of circular holes 31.

Figure 3:
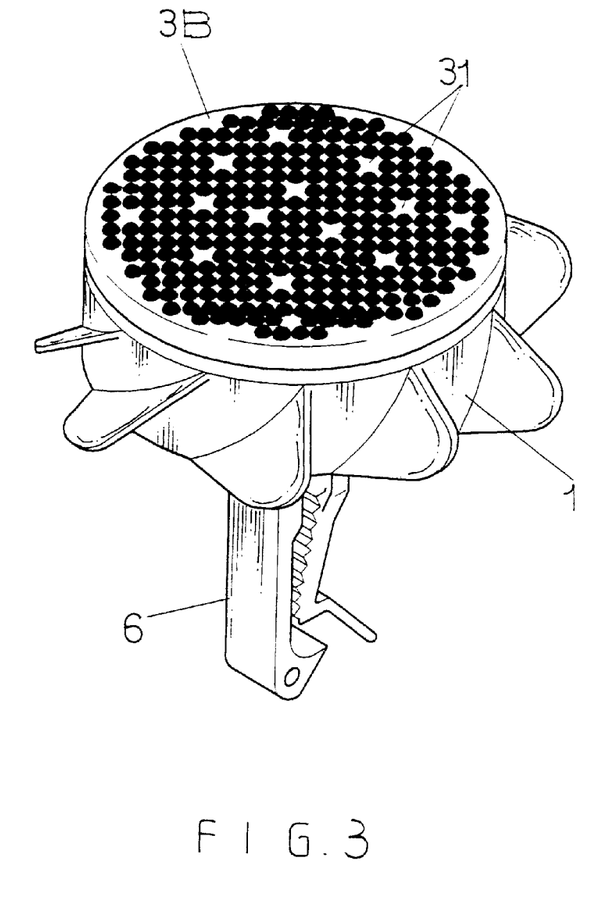
FIG. 3 is a perspective assembly view of an aromatic container of a third preferred embodiment in accordance with the present invention.

Referring to FIG. 3, another disk cover 3B can replace the ring 3 and the center cover 4. The disk cover 3B is disposed on the disk vessel 2. The disk cover 3B has a plurality of circular holes 31.

Figure 1B:
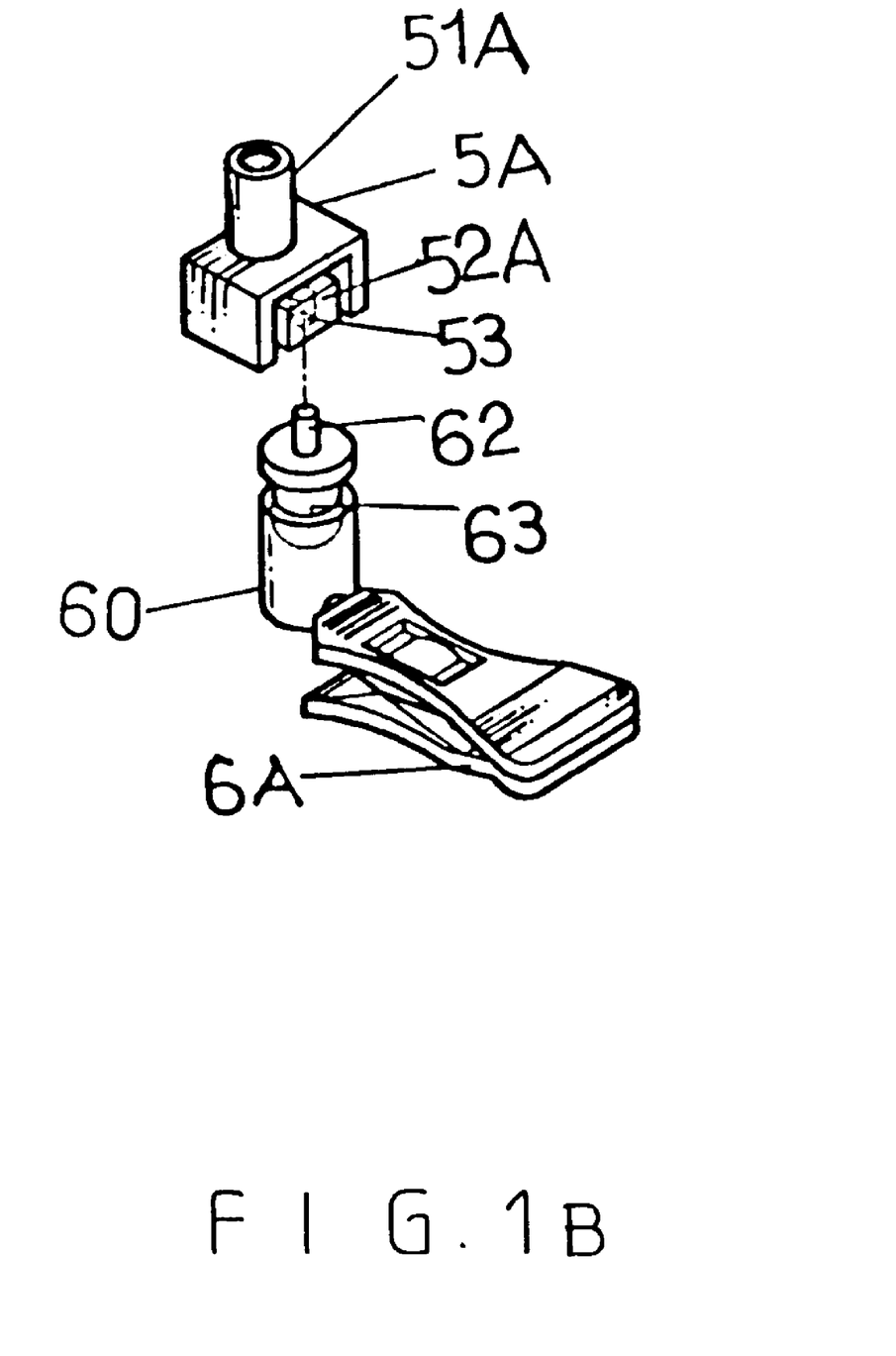
FIG. 1B is a perspective exploded view of a pivot seat and a clamp device of another preferred embodiment in accordance with the present invention.
Figure 5:
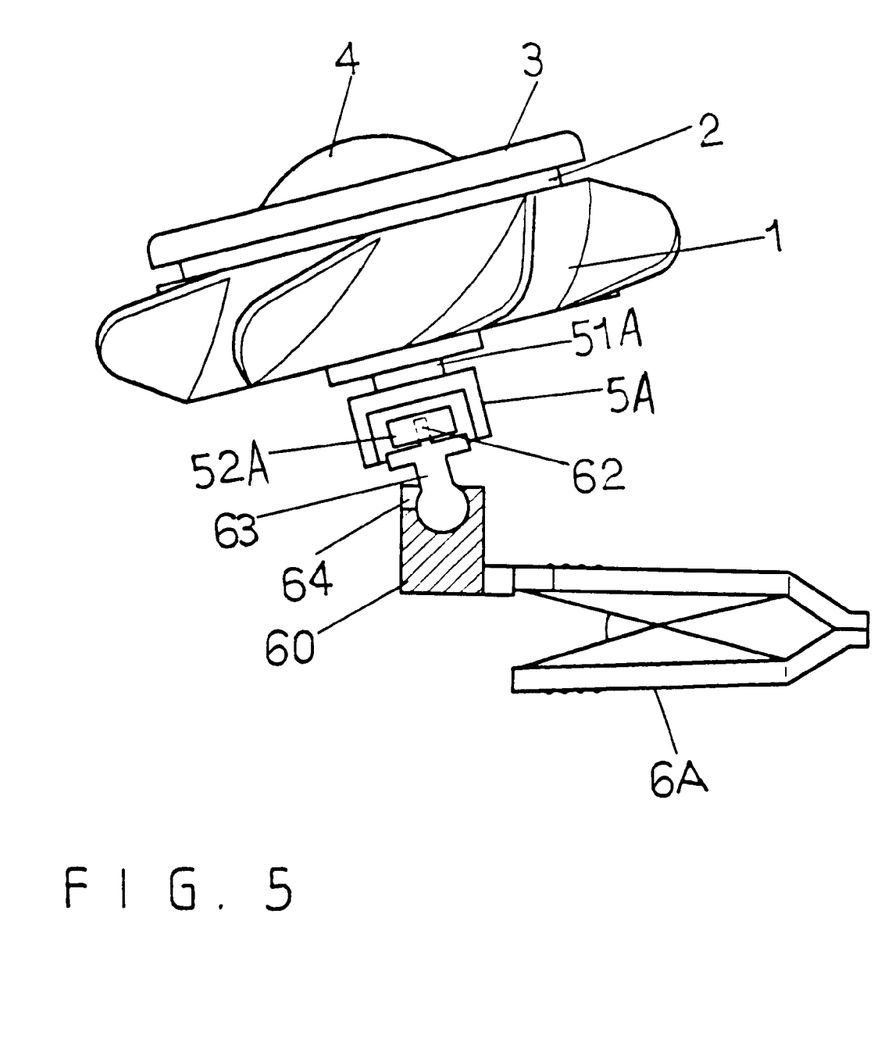
FIG. 5 is an elevational assembly view of an aromatic container of another preferred embodiment in accordance with the present invention.

Referring to FIGS. 1B and 5, another clamp device 6A can replace the first clamp device 6. The clamp device 6A has a sleeve 60, a rotating rod 63 inserted in the sleeve 60, and a pillar disposed on the rotating rod 63.

Another pivot seat 5A can replace the first pivot seat 5. The pivot seat 5A has a bottom hole 53, a block 52A, and a hollow post 51A inserted in the center hole 11.

The pillar 62 is inserted in the bottom hole 53. The rotating rod 63 can be rotated in the sleeve 60.

The aromatic container is placed near a fresh air inlet. Therefore, the aromatics can be evaporated with a flow of the fresh air.

The ring 3 can be removed. The user can refill aromatics in the disk vessel 2.

The present invention is not limited to the above embodiments but various modification thereof may be made. Furthermore, various changes in form and detail may be made without departing from the scope of the present invention.

I claim:

1. An aromatic container comprising:

a rotating device, a disk vessel disposed on the rotating device, a ring disposed on the disk vessel, a pivot seat engaging with the rotating device, and a clamp device engaging with the pivot seat, the ring having a plurality of columns, a plurality of circular apertures, and a center opening receiving a center cover, the disk vessel having a central threaded aperture, a plurality of recesses receiving aromatics, a plurality of vent apertures, and a plurality of round apertures formed on an edge of the disk vessel, the round apertures receiving the columns, the rotating device having a center hole, the pivot seat having a block, and a hollow post inserted in the center hole, the clamp device having a through hole receiving the block, and a bolt passing through the central threaded aperture, the center hole, and the hollow post to fasten the disk vessel, the rotating device, and the pivot seat together.

2. An aromatic container comprising:

a rotating device, a disk vessel disposed on the rotating device, a cover disposed on the disk vessel, a pivot seat engaging with the rotating device, and a clamp device engaging with the pivot seat, the disk vessel having a central threaded aperture, a plurality of recesses receiving aromatics, a plurality of vent apertures, and a plurality of round apertures formed on an edge of the disk vessel, the rotating device having a center hole, the pivot seat having a block, and a hollow post inserted in the center hole, and a bolt passing through the central threaded aperture, the center hole, and the hollow post to fasten the disk vessel, the rotating device, and the pivot seat together.

3. The aromatic container as claimed in claim 2, wherein the clamp device has a sleeve, a rotating rod inserted in the sleeve, and a pillar disposed on the rotating rod.

* * * * *